(12) United States Patent
Zurbriggen et al.

(10) Patent No.: US 8,496,962 B2
(45) Date of Patent: Jul. 30, 2013

(54) TRANS-ADJUVANT SYSTEM

(75) Inventors: Rinaldo Zurbriggen, Rainstrasse (CH); Andreas Kammer, Haberlimatteweg (CH)

(73) Assignee: Pevion Biotech, Ltd., Bern (CH)

( * ) Notice: Subject to any disclaimer, the term of this patent is extended or adjusted under 35 U.S.C. 154(b) by 1007 days.

(21) Appl. No.: 12/086,315

(22) PCT Filed: Dec. 15, 2006

(86) PCT No.: PCT/EP2006/012132
§ 371 (c)(1), (2), (4) Date: Aug. 27, 2009

(87) PCT Pub. No.: WO2007/068497
PCT Pub. Date: Jun. 21, 2007

(65) Prior Publication Data
US 2010/0015214 A1   Jan. 21, 2010

(30) Foreign Application Priority Data
Dec. 16, 2005 (EP) ..................................... 05027624

(51) Int. Cl.
*A61K 9/127* (2006.01)

(52) U.S. Cl.
USPC ........................................................ 424/450

(58) Field of Classification Search
None
See application file for complete search history.

(56) References Cited

U.S. PATENT DOCUMENTS

| | | | |
|---|---|---|---|
| 2003/0113347 A1 | 6/2003 | Cusi et al. | |
| 2010/0015214 A1* | 1/2010 | Zurbriggen et al. | 424/450 |

FOREIGN PATENT DOCUMENTS

| | | |
|---|---|---|
| WO | WO92/19267 | 11/1992 |
| WO | WO98/50071 | 12/1998 |
| WO | WO2004/045582 | 6/2004 |
| WO | WO2006/085983 | 8/2006 |

OTHER PUBLICATIONS

Gamvrellis, A. et al., "Vaccines that facilitate antigen entry into dendritic cells", 2004, Imm. and Cell Biol., vol. 82: pp. 506-516.*
Amacker et al., 2005, Int Immunol 17(6):695-704.
Schumacher et al., 2004, Vaccine 22:714-23.
Zurbriggen et al., 2000, Prog Lipid Res. 39(1):3-18.
Zurbriggen, 2003, Vaccine. 21(9-10):921-4.
Glüeck et al., "Verosomes, a new liposome-like vaccine delivery system" Drug Targeting and Delivery, Harwood Academic Publishers, Chur, CH 1997, pp. 101-122.
Kaneda et al., "Virosomes: evolution of the liposome as a targeted drug delivery system" Advanced Drug Delivery Reviews, Amsterdam, NL, vol. 43, 2000, pp. 197-205.
Adamina, et al., "Encapsulation into sterically stabilized liposomes enhances the immunogenicity of melanoma-associated Melan-A/MART-1 epitopes," British Journal of Cancer, 2004, 90:263-269.
Ball, "Quantitation of proteins by elution of Coomassie brilliant blue R from stained bands after sodium dodecyl sulfate-polyacrylamide gel electrophoresis" 1986, Anal Biochem 155(1):23-7.
Böttcher et al., "A rapid and sensitive sub-micro phosphorus determination." 1961 Anal Chim Acta 24:203-204.
Bron, et al., "Preparation, properties, and applications of reconstituted influenza virus envelopes (virosomes)." 1993, Methods Enzymol 220:313-331.
Daemen, et al., "Virosomes for Antigen and DNA delivery." 2005 Advanced Drug Delivery Reviews 57:451-463.
Felnerova et al., "Liposomes and virosomes as delivery systems for antigens, nucleic acids and drugs." 2004 Current Opinion in Biotechnology 15:518-529.
Gerhard, et al., "The analysis of the monoclonal immune response to influenza virus.II The antigenicity of the viral hemagglutinin." 1976, J Exp Med 144(4):985-995.
Gollins and Porterfield, "pH-dependent Fusion between the Flavivirus West Nile and Liposomal Model Membranes." 1986, The Journal of General Virology 67:157-166.
Monnard, et al., "Entrapment of nucleic acids in liposomes." 1997, Biochim Biophys Acta 1329(1):39-50.
Nussbaum, et al., "Reconstitution of Functional Influenza Virus Envelopes and Fusion with Membranes and Liposomes Lacking Virus Receptors." 1987, J Virol 61(7):2245-2252.
Oberholzer, et al., "Enzymatic reactions in liposomes using the detergent-induced liposome loading method." 1999, Biochim Biophys Acta 1416:57-68.
Schoen, et al., "Delivery of foreign substances to cells mediated by fusion-active reconstituted influenza virus envelopes (virosomes)." 1993, Journal of Liposome Research 3(3):767-792.
Skekel and Schild, "The polypeptide composition of influenza A viruses." 1971, Virology 44:396-408.
Stegman et al., "Membrane Fusion Mechanisms: The Influenza Hemagglutinin Paradigm and its Implications for Intracellular Fusion." 2000, Traffic 1:598-604.
Van Winden, "Freeze-drying of Liposomes: Theory and Practice." 2003, Methods in Enzymology 367:99-110.
Wagner, et al., "Enhanced protein loading into liposomes by the multiple crossflow injection technique." 2002, J. Liposome Res. 12(3):271-283.

* cited by examiner

*Primary Examiner* — Michael Burkhart
(74) *Attorney, Agent, or Firm* — Riverside Law LLP

(57) ABSTRACT

The present invention relates to a novel adjuvant system that generates an efficient immune response against antigens of various origins while reducing the risk of toxic side effects attendant to the use of known adjuvants. The novel adjuvant of the present invention comprises virosomes and allows antigenic molecules to be bound to or encapsulated in a variety of delivery vehicles which are easier to prepare for virosomes.

26 Claims, 7 Drawing Sheets

Figure 3

|  | Peptide [% of input] |
|---|---|
| Precipitate Peptide in CIRIV | ~88 |
| Precipitate Empty CIRIV & Peptide in Liposomes | ~0 |
| Control Peptid in CIRIV | 100 |

TRANS-ADJUVANT SYSTEM

CROSS-REFERENCE TO RELATED APPLICATIONS

This application is the U.S. national phase application filed under 35 U.S.C. §371 claiming benefit to International Patent Application No. PCT/EP2006/012132, filed on Dec. 15, 2006, which is entitled to priority under 35 U.S.C. §119(a) and §365(b), to European Patent Application No. 05027624.5, filed Dec. 16, 2005, each of which application is hereby incorporated herein by reference in its entirety.

FIELD OF THE INVENTION

The invention relates to the fields of immunology and vaccinology. Specifically, the invention relates to novel adjuvant systems that generate efficient immune responses against antigens of various origins.

BACKGROUND OF THE INVENTION

The last decade has seen great progress in therapeutic and prophylactic approaches based on vaccination against antigens present on tumor cells and infectious pathogens. Despite the advances made in the identification of new antigens and the elucidation of mechanisms that allow for targeted immune responses against such antigens, a number of challenges remain to be resolved. One obstacle, in particular, is the generation of sufficiently potent immune responses even after the identification of new antigens, as many promising antigenic targets have been shown to be only weakly immunogenic.

To elicit an immune response, antigens have to be taken up and processed by a special type of cell, the so-called antigen-presenting cells (APCs). The three cell types able to present antigens are dendritic cells, macrophages, and B-lymphocytes. The uptake is facilitated by phago- or endocytosis and the processing is done in vesicles or the cytosol. Key players in the presentation of the antigen on the cell surface are a class of proteins termed major histocompatibility complex proteins (MHC). These molecules are encoded by the most polymorphous gene family in the human genome located on chromosome 6 and can be subdivided into class I and II. The topology of both classes of molecules is such that they can bind and present as broad a spectrum of peptides 8 to 16 amino acids in length as possible. Thus, a very effective immunosurveillance is ensured. The copy number of a defined antigenic molecule on the surface of an antigen-presenting cell is quite low (about one hundred), given the total number of about ten thousand receptors, but this feature accounts for a very heterogeneous mixture of antigenic peptides on the surface of each APC.

MHC class I molecules bind and present samples of peptides, including endogenous as well as translated and processed viral or tumor antigens and activate the cellular, cytotoxic immune response via CD8+ (cytotoxic) T-cells. Autoimmunity against endogenous molecules is normally prevented by the negative selection process of the immune cells in the thymus, the bone marrow, and the lymphatic system. MHC class II molecules bind and present peptides, which are ingested from the immediate cellular environment and processed by a variety of enzymes in vesicles, generated by the fusion of lysosomes and phagosomes. Peptides bound to class II molecules activate CD4+ (helper) T-cells, which in turn activate B-cells, thus inducing the humoral immune response, and/or CD8+ T-cells, thus inducing a cellular immune response.

A peptide has the ability to provoke a specific cellular immune response if it is capable of binding to MHC molecules and has the ability to be recognized by CD8+ or CD4+ T-cells or it has the ability to induce a humoral response if it is recognized by a B-cell via membrane bound immunoglobulin. Immunogenicity of an antigen is defined by many variables including size, structure, stability, difference to endogenous molecules, adjuvant presence and the immune condition of the organism as well as other genetic factors. When the antigen is no foreign protein or peptide, it is normally not recognized by T-cells, since these cells are not present or are selected not to react with endogenous proteins, and its presentation in the MHC complex on the surface of an antigen-presenting cell is not sufficient to provoke an immune response.

The use of proteins or glycoproteins in the development of new and effective vaccines is controversial as, in several cases, it has proven to be either ineffective or hazardous to the inoculated organism. This property is due to a lack of immunogenicity based on a non-favorable size, structure, stability, or homology to endogenous proteins, or to the inclusion of non-protective epitopes. In addition, native peptides have a low systemic stability and are rapidly degraded by proteases. Another disadvantage is that it is not guaranteed that the peptide is capable of binding to major histocompatibility complex (MHC) proteins class I or II, which is absolutely necessary for the elicitation of an immune response.

Because such weak immune responses offer little clinical benefit, the development of effective immune response potentiating compounds to enhance the immunogenicity of target antigens has become a goal of increasing therapeutic and prophylactic importance.

Immune response potentiating compounds are classified as either adjuvants or cytokines. Adjuvants may enhance the immunological response by providing a reservoir of antigen (extracellularly or within macrophages), activating macrophages and stimulating specific sets of lymphocytes. Adjuvants of many kinds are well known in the art; specific examples include Freund's (complete and incomplete), components of the cells wall of mycobacterias (Bacillus calmette-guerin, *Mycobacterium vaccae, corynebacterium parvum*), lipopolysaccharides such as Lipid A, monophosphoryl Lipid A, LPS or LPS derivates or MF59 (Chiron), and various oil/water emulsions (e.g. IDEC-AF). Other currently used adjuvants include: mineral salts or mineral gels such as aluminium hydroxide, aluminium phosphate, and calcium phosphate, surface active substances such as lysolecithin, pluronic polyols, polyanions, keyhole limpet hemocyanins, and dinitrophenol, immunostimulatory molecules, such as saponins (QS-21 (SmithKline Beecham) ISCOMs), muramyl dipeptides and tripeptide derivatives, CpG dinucleotides, CpG oligonucleotides, lipopeptides/lipoproteins, cholera toxin and polyphosphazenes, particulate and microparticulate adjuvants, such as emulsions, cochleates, or immune stimulating complex mucosal adjuvants.

Cytokines are also useful in vaccination protocols as a result of lymphocyte stimulatory properties. Many cytokines useful for such purposes will be known to one of ordinary skill in the art, including interleukin-2 (IL-2), IL-12, GM-CSF, and many others.

Immunization strategies to efficiently prime CD8+ T cell responses have come into focus of research activity in current vaccinology. Recent advances in the development of potent adjuvants resulted in two main, alternative approaches, i.e. peptide- and DNA-based vaccine formulation. However, despite their promise as powerful adjuvants, the administration of both can exert toxic effects on the host, which limits their usefulness in the clinical context. It would thus be desirable to develop adjuvant systems that provide potent immune stimulation while reducing or eliminating the risk of toxic side effects.

WO 98/50071 discloses adjuvant properties of virus-like particles (VLPs), which enhance the humoral and/or cell-mediated immune response in vertebrates if administered with a selected antigen. VLPs are non-replicating empty viral shells composed of one or more capsid, coat, shell, surface and/or envelope proteins. According to the disclosure it was found that the selected antigen does not have to be entrapped in the VLP for the VLP to exert its adjuvant or coadjuvant effect.

European Patent No. 1550458 describes a method to enhance the specific immune response against an antigen, which is administered in a liposome together with a first conventional adjuvant, either also comprised in the first liposome or in a second liposome, by the coadministration of a second conventional adjuvant in free or liposomal form. The inventors found out that surprisingly the adjuvant action observed for two free adjuvants could be further enhanced if at least one of the adjuvants and the antigen was comprised in the same or separate liposomes.

WO 2004/045582 discloses a fusogenic vesicle containing encapsulated antigen. The fusogenic vesicle is the product of fusing liposomes with virosomes bearing hemagglutinin ("HA") fusion proteins from different virus strains. The fusion of liposomes and virosomes is triggered by conditions of low pH (about pH 4.5-5).

WO 2006/085983 discloses virus replicating particles ("VRPs") which can act as an adjuvant to enhance an immune response against an immunogen not presented or expressed by the virus. The inventors state that the adjuvant effect is dependent on the VRP's ability to replicate, meaning that the VRPs disclosed contain either unmodified or modified portions of a viral genome.

Schumacher et al. (Vaccine 22:714-723, 2004) found that Immunopotentiating reconstituted influenza virosomes (IRIV), the adjuvant capacity of which in the induction of humoral immune responses has been demonstrated before, are also capable to enhance the T cell-mediated immune response. More specifically, Schumacher and colleagues could show IRIV adjuvant activity in the induction of HLA class I restricted cytotoxic T lymphocytes (CTL) in vitro. This capacity was found to mainly rely on the stimulation of CD4+ T cell reactivity specific for viral proteins.

The adjuvant properties of IRIVs are well known in the art, for example from WO 92/19267, wherein an adjuvant effect of the IRIVs for an antigen coupled thereto is disclosed.

However, although the use of virosomes as adjuvants has a number of advantages, for example low toxicity and high immunogenicity, one of the problems in current virosome technology is the lack of methods for the efficient entrapment of a solute, e.g. protein, nucleic acid, or pharmaceutical drug. At the lipid concentration at which virosomes are produced (~1 mM lipid), and given their mean diameter of approximately 200 nm, less than 1% of the aqueous phase will be entrapped within the virosomes (Schoen et al., J. Liposome Res. 3: 767-792, 1993). Such low entrapment rates reduce virosome-mediated efficiency of antigen, drug, or gene delivery to cells. Thus, one of the problems in current virosome technology is the lack of methods for the efficient entrapment of a solute, e.g. protein, nucleic acid, or pharmaceutical drug.

Therefore, there exists still a need for efficient and cost-effective adjuvant systems to enhance the immunogenicity of otherwise weakly immunogenic antigenic molecules, preferably combined with safe and efficient delivery characteristics.

SUMMARY OF THE INVENTION

The present invention fulfills this need by the provision of novel adjuvant systems that reduce the risk of toxic side effects associated with the use of known adjuvants while providing powerful stimulation of immune responses against target antigens. These novel adjuvant systems are based on virosomes and are capable of eliciting strong immune responses against target antigens.

Additionally, the present invention circumvents the problems associated with virosome loading, as the inventors have found that the virosomes of the invention possess a trans-adjuvant effect. Said trans-adjuvant effect of the virosomes allows the antigenic molecules to be bound to or encapsulated in other delivery vehicles, which are easier to prepare, for example liposomes.

Thus, in a first aspect, the present invention relates to a pharmaceutical composition comprising a virosome, a liposome, and at least one antigenic molecule, wherein the pharmaceutical composition is maintained at physiological pH. The at least one antigenic molecule is neither bound, nor coupled, nor otherwise associated with the virosome, but preferably bound to or entrapped in said liposome. The antigen can be bound to the surface of the liposome for example via a lipophilic anchor molecule, or be encapsulated within the liposome using methods known to the person skilled in the art. The pharmaceutical composition of the invention is maintained at physiological pH. At this pH, the virosomes and liposomes of the pharmaceutical composition remain separate entities, i.e. they do not fuse with one another.

The antigen can be selected from any known antigen molecule and can for example be a nucleic acid, a peptide, a protein, a carbohydrate, a lipid, or any combination thereof, for example glycopeptides, lipopeptides, nucleopeptides and the like, as well as any derivative thereof. Specifically included are, by way of example, antigenic peptides, for example surface antigens of viruses or bacteria, bacterial toxins, and antigenic nucleic acid molecules.

The pharmaceutical compositions according to the invention can optionally further comprise excipients, auxiliaries, additives, solvents and other pharmaceutically acceptable substances known to the person skilled in the art.

In one preferred embodiment of the present invention, the utilized virosome is an immunopotentiating reconstituted influenza virosome (IRIV).

In another aspect, a virosome, a liposome, and at least one antigenic molecule are used for the manufacture of a pharmaceutical composition for the vaccination or immunization of a subject, wherein the pharmaceutical composition is maintained at physiological pH. Preferably, the at least one antigenic molecule is entrapped in or bound to said liposome.

A further aspect involves the use of a virosome, a liposome, and at least one antigenic molecule for the manufacture of a pharmaceutical composition for treating and/or preventing a disease or disorder in a subject in need thereof including but not limited to viral, bacterial, fungal, parasite and prion infectious diseases, wherein the pharmaceutical composition is maintained at physiological pH. Preferably, the at least one antigenic molecule is entrapped in or bound to said liposome.

The viral infectious disease may for example be chosen from AIDS, AIDS Related Complex, Chickenpox (Varicella), Common cold, Cytomegalovirus Infection, Colorado tick fever, Dengue fever, Ebola haemorrhagic fever, Epidemic parotitis, Genital warts, Hand foot and mouth disease, Hepatitis, Herpes simplex, Herpes zoster, HPV, Influenza (Flu), Lassa fever, Measles, Marburg haemorrhagic fever, Infectious mononucleosis, Mumps, Poliomyelitis, Progressive multifocal leukencephalopathy, Rabies, Rubella, SARS, Smallpox (Variola), Viral encephalitis, Viral gastroenteritis, Viral meningitis, Viral pneumonia, West Nile disease, Yellow fever. These and other viral diseases are caused by RSV, Polioviruses, Rubella virus, Dengue virus, Flaviviridae, Coronaviridae, Reoviridae, Rabies virus, Paramyxoviridae (e.g., mumps virus, measles virus, respiratory syncytial virus, etc.), orthomyxoviridae (e.g., influenza virus types A, B and C, etc.), simian immunodeficiency virus (SIV), HAV, HBV, HCV, HDV, HEV, HPV, HSV, HIV, CMV, EBV, Polio virus, varicella.

The bacterial infectious disease may for example be chosen from Anthrax, Bacterial Meningitis, Brucellosis, Campylobacteriosis, Cat Scratch Disease, Cholera, Diphtheria, Epidemic Typhus, Gonorrhea, Impetigo-Legionellosis, Leprosy (Hansen's Disease), Leptospirosis, Listeriosis, Lyme Disease, Melioidosis, meningitis, MRSA infection, Nocardiosis, Pertussis (Whooping Cough), Plague, Pneumococcal pneumonia, Psittacosis, Q fever, Rocky Mountain Spotted Fever (RMSF), Salmonellosis, Scarlet Fever, Shigellosis, Syphilis, Tetanus, Trachoma, Tuberculosis, Tularemia, Typhoid Fever, Typhus and Urinary Tract Infections. These and other bacterial diseases are caused by *Corynebacterium diphtheriae*, *Clostridium tetani*, *Bordetella pertussis*, *Neisseria meningitidis*, including serotypes Meningococcus A, B, C, Y and W135 (MenA, B, C, Y and W135 *Haemophilus influenza* type B (Hib), and *Helicobacter pylori*).

The fungal infectious disease may for example be chosen from Aspergillosis, Blastomycosis, Candidiasis, Coccidioidomycosis, Cryptococcosis, Histoplasmosis and Tinea pedis.

The parasitic infectious disease may for example be chosen from African trypanosomiasis, Amebiasis, Ascariasis, Babesiosis, Chagas Disease, Clonorchiasis, Cryptosporidiosis, Cysticercosis, Diphyllobothriasis, Dracunculiasis, Echinococcosis, Enterobiasis, Fascioliasis, Fasciolopsiasis, Filariasis, Free-living amebic infection, Giardiasis, Gnathostomiasis, Hymenolepiasis, Isosporiasis, Kala-azar, Leishmaniasis, Malaria, Metagonimiasis, Myiasis, Onchocerciasis, Pediculosis, Pinworm Infection, Scabies, Schistosomiasis, Taeniasis, Toxocariasis, Toxoplasmosis, Trichinellosis, Trichinosis, Trichuriasis and Trypanosomiasis.

The prion infectious disease may for example be chosen from transmissible spongiform encephalopathy, Bovine spongiform encephalopathy, Creutzfeldt-Jakob disease and Kuru.

In a preferred embodiment of the invention the disease or disorder to be treated with the pharmaceutical composition of the invention includes, but is not limited to, infectious diseases such as those caused by HAV, HBV, HCV, HDV, HEV, HPV, HSV, HIV, CMV, EBV, SIV, Polio virus, varicella, *Mycoplasmal* and other bacteria, and *M. pneumoniae*.

Another disease or disorder preferably treated with the pharmaceutical composition of the invention is cancer.

Said subject may be a mammal, and preferably is a human.

Also encompassed by the present invention are methods for the preparation of a pharmaceutical composition according to the invention, comprising the steps of providing a virosome as an adjuvant and an antigenic molecule entrapped in or bound to a liposome, and forming a mixture thereof in a pharmaceutically acceptable excipient or solvent maintained at physiological pH.

Another aspect of the invention relates to a kit of parts comprising a virosome, a liposome, and at least one antigenic molecule, wherein the kit additionally comprises means for maintaining the virosome, the liposome and/or the at least one antigenic molecule at physiological pH. In one specific embodiment, the antigenic molecule may be entrapped in or bound to the liposome. The means for maintaining the virosome, the liposome and/or the at least one antigenic molecule at physiological pH may be in the form of an appropriately buffered solution(s) or may be in the form of appropriate salts, either together with or apart from the remaining components of the kit. All said compounds may be stored in separate vessels and may be lyophilized. In case one or more of the kit compounds are lyophilized the solvent for the solvation may be included in the kit.

Figure 1:
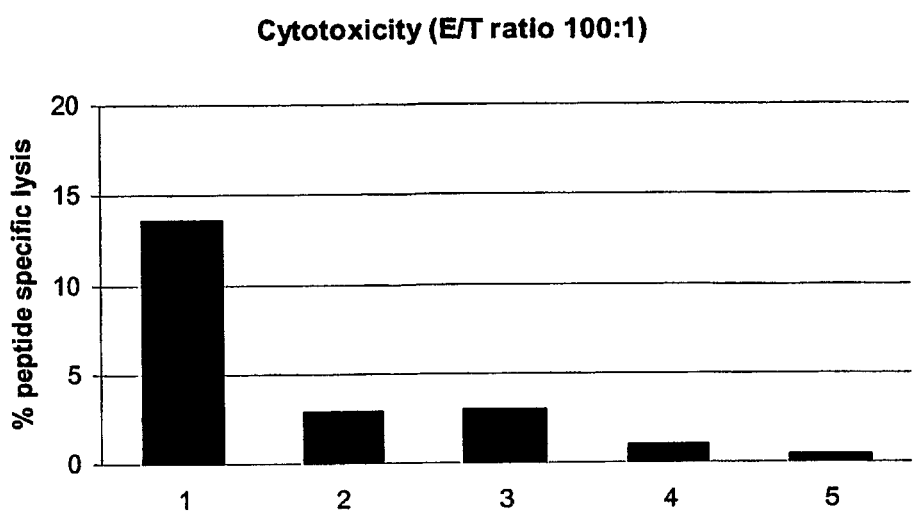
FIG. 1.
Figure 1:
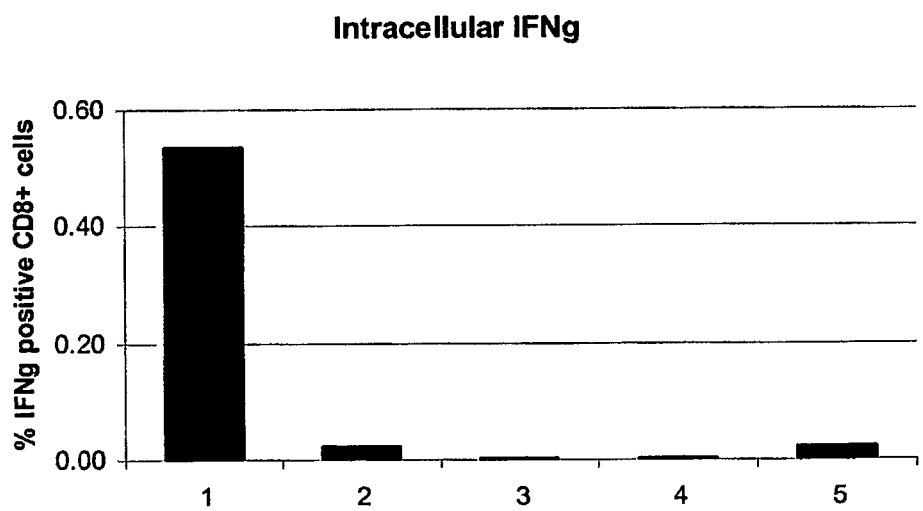
Figure 2:
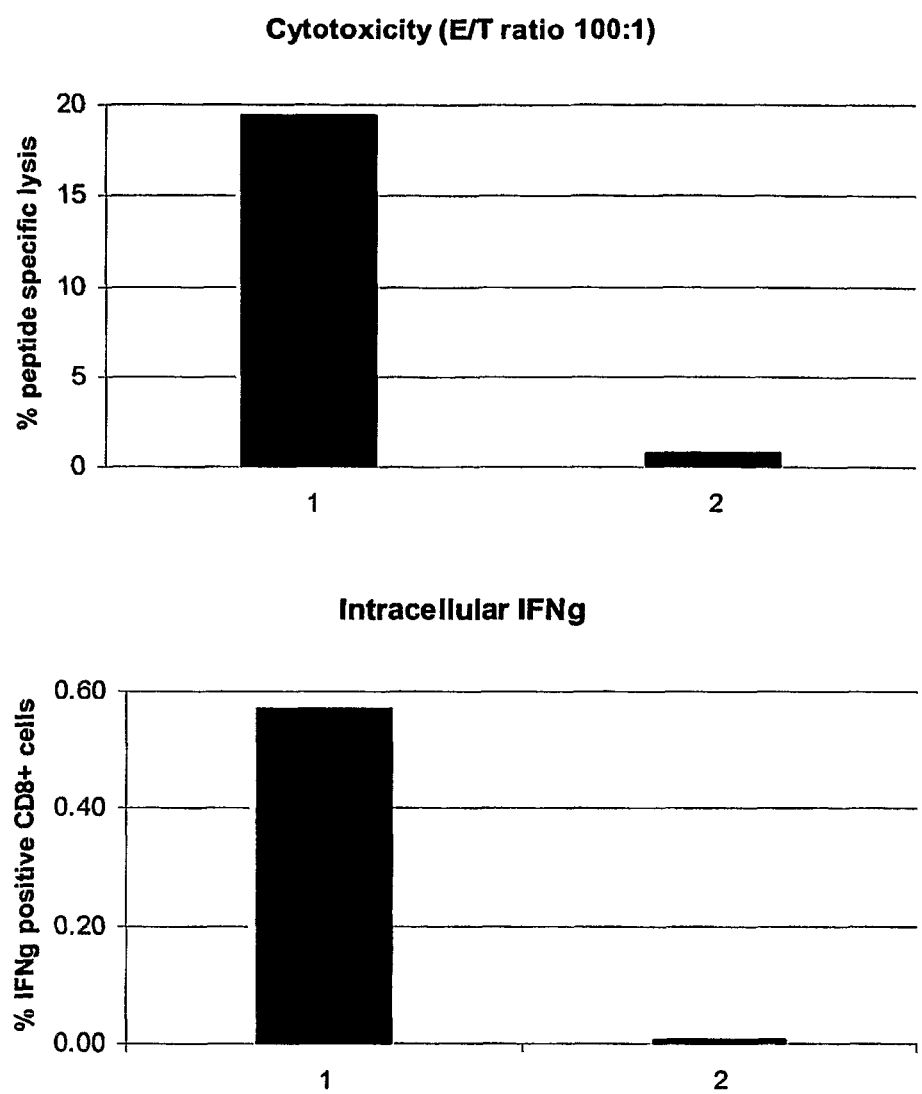
Figure 4:
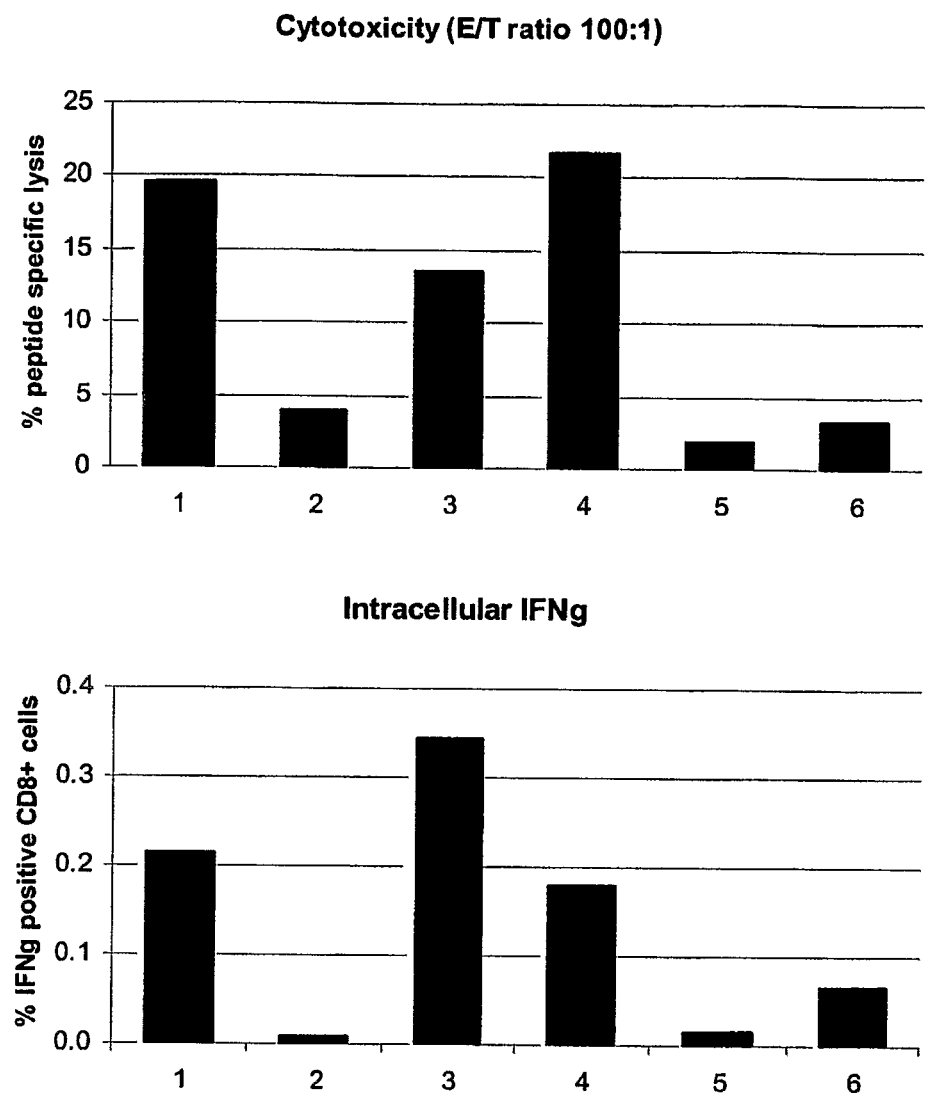
Figure 5:
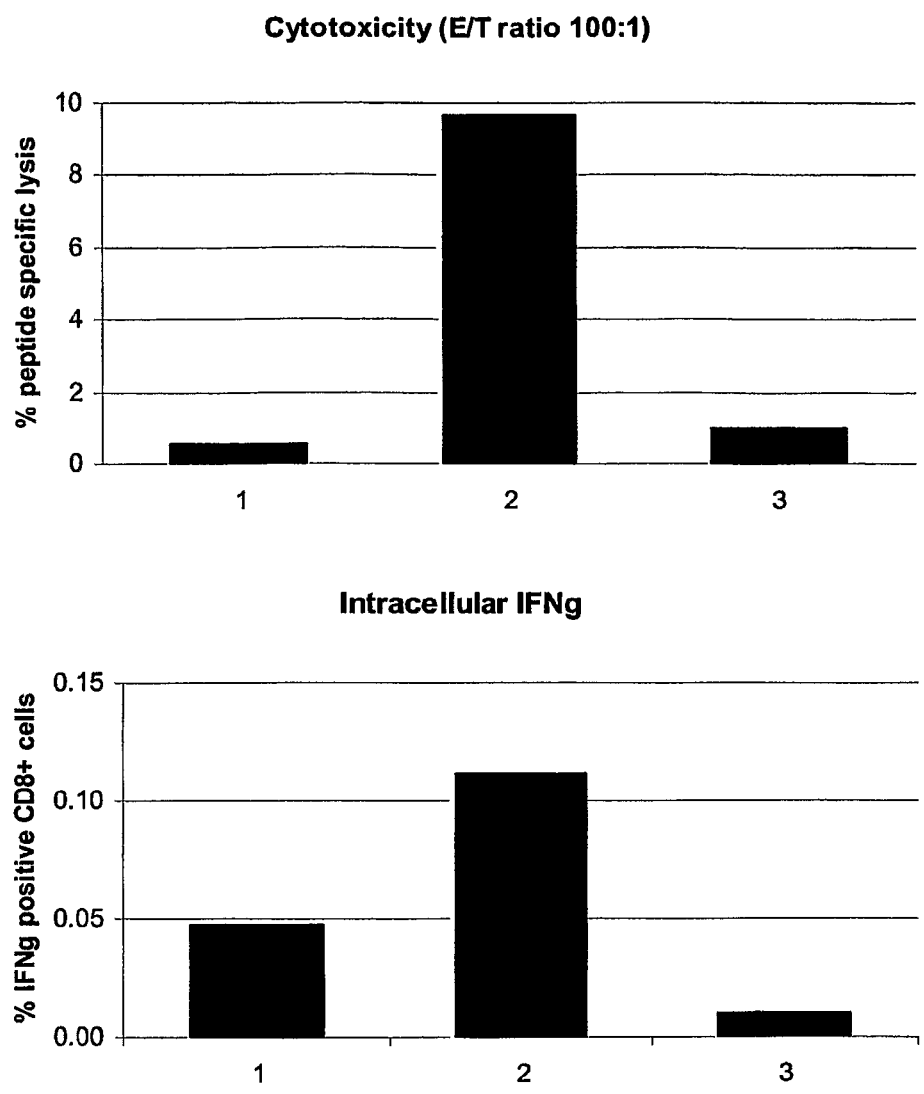
Figure 6:
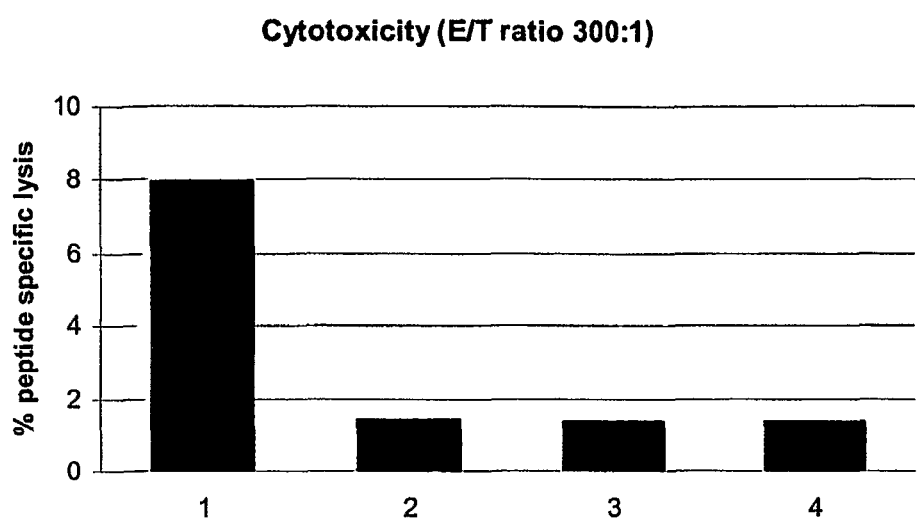
Figure 7:
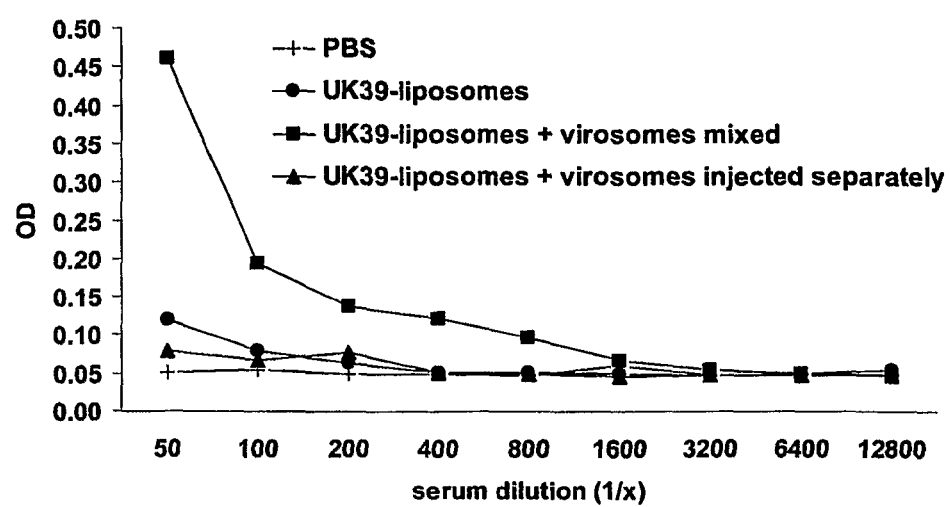

IRIV as trans-adjuvant for peptides; Induction of CD8+ cells

This figure demonstrates the immunogenicity of HCV core 132-peptide-loaded liposomes (i.e. liposomes encapsulating HCV core 132-peptide) mixed with empty virosomes. HLA-A2 tg HHD mice were immunized twice s.c. at a 3-week interval with 200 μg peptide per dose in different formulations:

(1) Core 132 peptide in liposomes+empty virosomes
(2) Core 132 peptide in liposomes
(3) Core 132 peptide+empty virosomes
(4) Core 132 peptide
(5) Empty virosomes The spleen cells were isolated 2 weeks after boost. Graphs show the peptide specific lysis at an E/T ratio of 100:1 after 5-day in vitro restimulation (upper panel) and frequency of peptide specific IFN gamma producing CD8+ T cells.

FIG. 2:

IRIV as trans-adjuvant for peptides; Induction of CD8+ cells

This figure demonstrates the immunogenicity of HCV core 35-peptide-loaded liposomes (i.e. liposomes encapsulating HCV core 35-peptide) mixed with empty virosomes. HLA-A2 tg HHD mice were immunized twice s.c. at a 3-week interval with 200 μg peptide per dose in different formulations:

(1) Core 35 peptide in liposomes+empty virosomes
(2) Empty virosomes

The spleen cells were isolated 2 weeks after boost. Graphs show the peptide specific lysis at an E/T ratio of 100:1 after 5-day in vitro restimulation (upper panel) and frequency of peptide specific IFN gamma producing CD8+ T cells.

FIG. 3:

Non-interaction of virosomes and liposomes with one another in solution at physiological pH This figure demonstrates that virosomes and liposomes do not physically interact with each other, i.e. remain separate from one another, at physiological pH. The following were precipitated in separate experiments with streptavidin paramagnetic beads:

Chimeric IRIVs ("CIRIV") encapsulating peptide and bound to biotin, as a comparative control (top bar in the figure);

Liposomes encapsulating peptide mixed with empty CIRIVs bound to biotin (middle bar in the figure, which is not visible as no peptide could be precipitated);

Equal amounts of peptide were used in the CIRIVs as in the liposomes. The peptide in the precipitate was quantified by RP-HPLC. As a control the peptide content of CIRIV encapsulating peptide and bound to biotin was quantified without immunoprecipitation (third bar in the figure).

FIG. 4:

IRIV as trans adjuvant for peptides; Induction of CD8+ cells

This figure demonstrates the immunogenicity of HCV core 132-peptide-loaded liposomes (i.e. liposomes encapsulating HCV core 132-peptide) mixed with empty virosomes. HLA-A2 tg HHD mice were immunized twice s.c. at a 3-week interval with 200 μg peptide per dose in different formulations:

(1) Core 132 peptide in liposomes+empty virosomes (mixed and then injected)
(2) Core 132 peptide in liposomes+empty virosomes (injected seperately at different sites)
(3) Core 132 peptide in chimeric virosomes (for comparative purposes)
(4) Core 132 peptide in chimeric virosomes+empty liposomes (mixed and then injected) (for comparative purposes)
(5) Core 132 peptide in liposomes
(6) Empty virosomes The spleen cells were isolated 2 weeks after boost. Graphs show the peptide specific lysis at an E/T ratio of 100:1 after 5-day in vitro restimulation (upper panel) and frequency of peptide specific IFN gamma producing CD8+ T cells (lower panel).

FIG. 5:

IRIV as trans-adjuvant for proteins; Induction of CD8+ cells

This figure demonstrates the immunogenicity of Ovalbumin protein-loaded liposomes (i.e. liposomes encapsulating ovalbumin protein) mixed with empty virosomes. C57Bl/6 mice were immunized twice s.c. at a 3-week interval with 200 μg protein per dose in different formulations:

(1) Ovalbumin protein in liposomes
(2) Ovalbumin protein in liposomes+empty virosomes
(3) Empty virosomes The spleen cells were isolated 2 weeks after boost. Graphs show the OVA 257 peptide specific lysis at an E/T ratio of 100:1 after 5-day in vitro restimulation (upper panel) and frequency of OVA 257 peptide specific IFN gamma producing CD8+ T cells (lower panel).

FIG. 6:

IRIV as trans-adjuvant for peptides; This figure demonstrates the immunogenicity of HCV core 132-peptide-loaded liposomes (i.e. liposomes encapsulating HCV core 132-peptide) mixed with empty virosomes, in comparison with a mixture of liposomes and hepatitis B surface antigen ("HBsAg"). The virosome shows a trans adjuvant effect while the HBsAg particle does not. HLA-A2 tg HHD mice were immunized twice s.c. at a 3-week interval with 200 μg peptide per dose in different formulations:

(1) Core 132 peptide in liposomes+empty virosomes
(2) Core 132 peptide in liposomes+HBsAg
(3) Core 132 peptide in liposomes
(4) no immunization The spleen cells were isolated 2 weeks after boost. Graphs show the peptide specific lysis at an E/T ratio of 300:1 after 5-day in vitro restimulation.

FIG. 7:

IRIV as trans adjuvant for peptides: Induction of antibody response with UK39 peptide This figure demonstrates the immunogenicity of UK39-peptide bound to liposomes mixed with empty virosomes. Balb/c mice were immunized three times i.m. at a 3-week interval with 5 μg peptide per dose in different formulations:

(1) UK39-peptide bound to liposomes+empty virosomes (mixed and then injected)
(2) UK39-peptide bound to liposomes+empty virosomes (injected seperately at different sites)
(3) UK39-peptide bound to liposomes Blood was taken 2 weeks after the last immunization and UK39-specific antibodies were analyzed in by ELISA. Graphs show optical density at different serum dilutions. PBS: PBS instead of serum was used for dilution (negative control).

TABLE 1

Amount of peptide encapsulated in liposomes

| Sample | Conc [μg/mL] |
| --- | --- |
| Core132-Liposomes without purification | 5000 |
| Core132-Liposomes after gelfitration (G50) | 833 |
| Core132-Liposomes after gelfitration (G50) and after proteinase K digestion | 820 |
| Core132 Peptide (0.2 mg/mL) | 220 |
| Empty Liposomes | 0 |
| Empty Liposomes & Core132 Peptide (0.2 mg/mL) without purification | 210 |
| Empty Liposomes & Core132 Peptide (0.2 mg/mL) after gelfiltration (G50) | 5 |

This table shows that a large amount of peptide is encapsulated into liposomes. For quantification of encapsulated peptide, a fraction of liposomes were loaded on freshly prepared, PBS-equilibrated 1 ml Sephadex G50 Coarse gel-filtration spin columns. Vesicles with encapsulated peptide were obtained after centrifugation of the spin column at 300×g for 2 min, as the non-encapsulated peptide was retarded in the column. For spiking experiments, a defined amount of peptide was added to empty liposomes before purification. In some samples not encapsulated peptide was digested with proteinase K. The peptide was quantified by RP-HPLC.

TABLE 2

Amount of peptide encapsulated in liposomes or virosomes

| Particle type | Particle diameter | Encapsulated peptide[a] |
| --- | --- | --- |
| Liposomes | up to 1.2 μm | 50-75% |
| Homogenised Liposomes | 0.2 μm | 30-40% |
| Homogenised Virosomes | 0.2 μm | 30-40% |

[a]in % of starting material. Data represent the range determined from at least 5 separate preparations.

This table shows the amount of HCV Core 132 peptide encapsulated into liposomes or, as a comparison, virosomes. For quantification of encapsulated peptide, a fraction of liposomes or virosomes were loaded on freshly prepared, PBS-equilibrated 1 ml Sephadex G50 Coarse gel-filtration spin columns. Vesicles with encapsulated peptide were obtained after centrifugation of the spin column at 300×g for 2 min, as the non-encapsulated peptide was retarded in the column. The peptide was quantified by RP-HPLC.

TABLE 3

Dependency of immunogenicity on concentration of hemagglutinin

| Vaccine | Amount of influenza hemagglutinin | Responder[a] |
| --- | --- | --- |
| Core 132 peptide in liposomes + virosomes | 150 μg | 83% (5/6) |

TABLE 3-continued

Dependency of immunogenicity on concentration of hemagglutinin

| Vaccine | Amount of influenza hemagglutinin | Responder[a] |
|---|---|---|
| Core 132 peptide in liposomes + virosomes | 50 µg | 33% (2/6) |
| Core 132 peptide in liposomes + virosomes | 15 µg | 40% (2/5) |
| Core 132 peptide in liposomes + virosomes | 5 µg | 17% (1/6) |
| Core 132 peptide in liposomes | 0 µg | 17% (1/6) |

[a]Percentage of immunized mice developing a positive immune response against Core 132 determined by measuring frequency of peptide specific IFN gamma producing CD8+ T cells. In brackets: responding mice/immunized mice.

This table demonstrates that the immunogenicity of HCV core 132-peptide-loaded liposomes (i.e. liposomes encapsulating HCV core 132-peptide) mixed with empty virosomes is dependent on the amount of hemagglutinin. HLA-A2 tg HHD mice were immunized subcutaneously (s.c.) with 100 µl of liposomes with encapsulated peptide; or liposomes with encapsulated peptide mixed with different amounts of empty virosomes. Mice received 2 injections at a 3-week interval and the response was analyzed 2 weeks after the last injection.

DETAILED DESCRIPTION OF THE INVENTION

The present invention provides novel adjuvant systems based on virosomes that are capable of eliciting a strong immune response against target antigens of choice.

Virosomes are known to have an adjuvant effect if an antigenic molecule is bound to or entrapped in the virosome (Zurbriggen Vaccine. 2003 14; 21(9-10):921-4). However, all prior art shows that the antigenic molecule has to be physically associated with the virosome (Zurbriggen et al. Progr. Lipid Res. 2000 39(1):3-18; Amacker et al., Int Immunol. 2005 17(6):695-704). Surprisingly, the inventors of the present invention have determined that virosomes can also be used to potentiate immune responses against a desired antigenic molecule in the presence of a liposome, even if the antigenic molecule is not physically associated with the virosome. Surprisingly, this trans-adjuvant effect of the virosomes is particularly pronounced if the antigen is combined with liposomes, meaning encapsulated therein or inserted in (i.e. bound to) the lipid layer of the liposome, although virosomes and liposomes do not physically interact with each other; at physiological pH the virosomes and peptide-associated liposomes remain separate from one another.

Thus, in a first aspect the present invention is directed to a pharmaceutical composition comprising an immunostimulatory virosome and further comprising at least one antigenic molecule and a liposome, wherein the pharmaceutical composition is maintained at physiological pH. The at least one antigenic molecule is preferably entrapped (i.e. encapsulated) in or bound to the liposome.

The pharmaceutical compositions of the invention are advantageous over the prior art, as the virosomes used for their trans-adjuvant effect are versatile with regard to lipid composition, are highly immunogenic and can be readily produced in vitro by methods known in the art. These features clearly distinguish the virosomes from VLPs and other vesicle-based adjuvants.

Further, the fact that the virosomes and liposomes of the pharmaceutical composition exist as separate entities at physiological pH, i.e. do not fuse with one another, implies great flexibility in the preparation of the pharmaceutical composition for a wide variety of different therapeutic and/or prophylactic applications. For instance, pre-prepared stores of virosomes can be added in varying amounts to liposome-antigen mixtures which have already separately prepared according to the requirements of a particular therapeutic or prophylactic application. Furthermore, once formed, the peptide-liposome:virosome ratio can be further tuned as needed by addition of more of one or the other component.

The present invention overcomes the problems and disadvantages of antigen entrapping connected to the in vivo production systems applied for the production of VLPs. The entrapping of antigenic molecules into virosomes was improved in recent years (Amacker et al., supra), but has still not reached the efficiency and simplicity of entrapping such molecules in liposomes. Therefore a further advantage of the present invention is that antigenic molecules can be encapsulated in liposomes easily and in high concentration, employing methods known to the person skilled in the art.

In the present invention the terms "antigenic molecule", "antigen", or "target antigen" are used interchangeably and herein refer to a molecule against which an immune response is desired. This molecule can be selected from a group including, but not limited to, peptides, proteins, lipids, mono-, oligo- and polysaccharides, glycopeptides, carbohydrates, lipopeptides, bacterial or viral pathogens and toxins, other small immunogenic molecules and DNA/RNA coding for such molecules or, more generally, an immunogenic molecule derived, for example, from a pathogen or malignant cell against which an immune response is desired and whose immunogenicity can be enhanced or potentiated by the adjuvants disclosed herein. Target antigens of interest include tumor-specific and tumor-associated antigens, as well as antigens from bacteria, viruses, parasites and other infectious organisms, all of which are well known in the art. Examples for antigenic molecules are peptide-based T-cell antigens and B-cell antigens. Preferred examples for antigenic molecules are HCV-based T-cell antigens, tumor-associated antigens, pertussis toxin, cholera toxoid and malaria, RSV and peptide antigens associated with Alzheimers disease (in particular the beta-amyloid). Antigenic peptides of the present invention may be produced by chemical synthesis, or they may be of natural or recombinant origin. Such peptides may be recombinantly produced using a nucleic acid molecule encoding the peptide.

"Pharmaceutical composition" refers to a composition which is suitable for administration as part of a regimen of treating and/or preventing a disease or condition. As such, the term "pharmaceutical composition" includes both therapeutic and prophylactic pharmaceutical compositions. Also included in the term "pharmaceutical composition" are compositions which are immunogenic in nature, meaning that they result in an immune response in a host to which the pharmaceutical composition is administered. As such, "pharmaceutical composition" as used herein encompasses vaccines.

"Physiological pH" refers to pH values typically existing in vivo in humans. In the broadest sense, "physiological pH" describes a pH range of about 6.5-8.0 inclusive. Preferably, "physiological pH" refers to pH 6.8-7.5 inclusive. Particularly, "physiological pH" may refer to pH 6.8, 6.9, 7.0, 7.1, 7.2, 7.3, 7.4 or 7.5.

"Immunogenic" refers to the ability of a molecule to elicit an immune response in an organism inoculated therewith.

The term "adjuvant" refers to a substance distinct from target antigen that is capable of enhancing or potentiating immune effector cell activation.

The term "adjuvant systems" is used herein to denote the combination of immunostimulatory compounds, such as the virosomes of the present invention, with target antigens to potentiate the immunostimulatory effect that each component of the system would exert if used by itself, as well as their combination with a suitable delivery system, such as liposomes, which may further increase the immune stimulatory effect of the compositions.

In the context of the present invention, the expression "trans-adjuvant" refers to an immunostimulating compound capable of eliciting or enhancing the immune response against an antigen not associated therewith. "Not associated therewith" means that the antigen is neither coupled, bound, conjugated, nor otherwise linked to the trans-adjuvant. "Not associated therewith" also means that the antigen is neither encapsulated nor entrapped in the trans-adjuvant.

The term "potentiating" or "immunopotentiating" is used herein to refer to an adjuvant or enhancing effect on immune functions which may occur through stimulation of immune effector cells and may lead to destruction or clearance of antigen-bearing pathogens or malignancies, and/or to immunity thereto.

"Virosomes", as used herein, are reconstituted viral envelopes which can be derived from a variety of viruses but which lack the infectious nucleocapsids and the genetic material of the source virus. Virosomes consist of a mixture of membrane lipids either of viral or non-viral origin and one or more viral envelope proteins. These envelope proteins account for the virosomal functionality, so that their membrane fusion activity closely mimics the well-defined low-pH-dependent membrane fusion activity of the intact virus, which is solely mediated by the viral fusion protein. Like viruses, virosomes are rapidly internalized by receptor-mediated endocytosis. In contrast to viral systems, virosomes are safe, since the infectious nucleocapsid of the virus has been removed. So far, virosomes are mainly used as vaccines by incorporating antigen onto the surface or into the lumen of the virosomes. In contrast to virus-like particles (VLPs), virosomes do not form spontaneously upon recombinant expression of the protein in an appropriate expression system but are the result of a controlled in vitro process, which allows large-scale industrial production of virosomes. The resulting virosomes contain a lipid bilayer composed mainly of synthetic lipids, whereas VLPs are made of cellular lipids and form most of the time no bilayers. Furthermore, in case of virosomes the content of the single components i.e. lipids, virus proteins can be varied according to the requirements for the final product. Due to the ease of their production and their versatility, the virosomes utilized in the present invention are therefore far more sophisticated than the VLPs known in the art.

The terms "encapsulated", "loaded into", "-loaded" and "entrapped" are used interchangeably in the present invention and refer to the localization of an antigen or any other suitable substance in the lumen of a virosome, liposome, or any other delivery vehicle/carrier having such a lumen.

Most preferably the virosomes utilized in the present invention are synthetic virosomes termed Immunopotentiating Reconstituted Influenza Virosomes (IRIVs). IRIVs are spherical, unilamellar vesicles with a mean diameter of 150 nm and comprise a double lipid membrane, consisting essentially of phospholipids, preferably Phosphatidylcholines (PC) and Phosphatidylethanolamines (PE). IRIVs contain the functional viral envelope glycoproteins hemagglutinin (HA) and neuraminidase (NA) intercalated in the phospholipid bilayer membrane. The biologically active HA not only confers structural stability and homogeneity to virosomal formulations but also significantly contributes to the immunological properties by maintaining the fusion activity of a virus.

Optionally, the IRIVs of the instant invention comprise hemagglutinin molecules of more than one virus strain, thus forming chimeric IRIVs ("CIRIVs").

In another preferred embodiment, the virosomes of the invention comprise cationic membrane lipids to further enhance the adjuvant properties and allow lyophilization of the virosomes. The cationic membrane lipids are preferably cationic cholesterol derivatives, more preferably DC-Chol (cholesteryl N-(dimethylammonioethyl) carbamate chloride) and/or TC-Chol (cholesteryl N-(trimethylammonioethyl) carbamate chloride).

The invention takes advantage of the fact that liposomes, which can be prepared at very high lipid concentrations, have high encapsulation efficiencies. Thus, the invention provides a pharmaceutical composition which combines the high loading capacity of liposomes with the immunopotentiating effect of virosomes, resulting in the efficient association, e.g. entrapment of solutes, like peptides, proteins, glycoproteins/peptides, carbohydrates or nucleic acids, and the like, within functional liposomes that are capable of delivering immunologically active substances to cells. At the same time, the pharmaceutical composition elicits a potent immune response against the associated, e.g. entrapped antigen by virtue of the trans-adjuvant activity of the virosomes.

Accordingly, in a preferred embodiment of the invention, the antigen is loaded into, or encapsulated by, liposomes. The liposomal lipids, which are used in the present invention, are preferably selected from the group consisting of cationic lipids, synthetic lipids, glycolipids, phospholipids cholesterol, or derivatives thereof. Phospholipids comprise preferably phosphatidylcholine, sphingomyelin, phosphatidylethanolamine, phosphatidylserine, phosphatidylglycerol, phosphatidic acid, cardiolipin, and phosphatidylinositol with varying fatty acyl compositions. Cationic lipids are preferably selected from the group consisting of DOTMA (N-[(1-(2,3-dioleyloxy)propyl]-N,N,N-trimethylammonium chloride), DOTAP (N-[1-(2,3-dioleoyloxy)propyl]-N,N,N-trimethylammonium chloride, DODAC (N,N-dioleyl-N,N,-dimethylammonium chloride), DDAB (didodecyldimethylammonium bromide), TC-Chol (cholesteryl N-(trimethylammonioethyl)carbamate chloride), DC-Chol (cholesteryl N-(dimethylammonioethyl)carbamate chloride), or other cationic cholesterol derivatives, and stearylamine or other aliphatic amines and the like. They are generally formulated as small unilamellar liposomes in a mixture with DOPE (dioleoylphosphatidyl ethanolamine) that is widely used as helper lipid to facilitate disruption of the endosomal membrane. Most preferably the liposomal lipids of the liposomes comprise phosphatidylglycerol and phosphatidylethanolamine, more preferably 1,2-dipalmitoyl-sn-glycero-3-phospho-rac-(1-glycerol) (PG) and 1,2-dioleyl-sn-glycero-3-phosphatidylethanolamine (DOPE).

Encapsulation of at least one antigenic substance, such as a protein, peptide, glycopeptide, glycoprotein, carbohydrate, nucleic acid, and the like into liposomes can be performed by any method known in the art, including the procedures described in Monnard et al., Biochim. Biophys. Acta 1329: 39-50, 1997, in Wagner et al., J. Liposome Res., 12(3) 271-283, 2002, or in Oberholzer et al., Biochim. Biophys. Acta 1416: 57-68, 1999, among many other well known methods. In a preferred embodiment of the invention, high liposomal encapsulation efficiencies are achieved by the freeze/thaw technique used to prepare pure lipid vesicles. With this method, approximately 50% of the initial amount of a linearized plasmid over 3 kb can be entrapped within large unilamellar vesicles (LUVs) consisting preferably of 1-palmitoyl- 2-oleoyl-sn-glycero-3-phosphocholine (POPC)/didodecyl-dimethylammonium bromide (DDAB) (Monnard et al., Biochim. Biophys. Acta 1329: 39-50, 1997).

The at least one antigenic molecule is entrapped in or bound to the liposome. In one embodiment of the invention, the at least one antigenic molecule bound to the liposome is conjugated to a lipid or lipophilic moiety, so that said lipid or lipophilic moiety may be inserted in the liposomal lipid layer in order to present the antigenic molecule on the liposome surface. Said lipid or lipophilic moiety can be any fatty acid, for example myristoleic acid or lauric acid, an isoprenoid, for example farnesyl or geranylgeranyl, a fatty alcohol, for example lauryl or myristyl alcohol, glykosylphosphatidylinositol, or any other suitable molecule known to those skilled in the art.

The virosomes of the invention comprise fusion-active membrane-bound proteins, for example hemagglutinin and/or neuraminidase, and membrane lipids, for example phosphatidylcholine, phosphatidylethanolamine, phosphatidylserine, and/or cholesterol derivatives. In the most preferred embodiment, the virosomes further comprise a cationic lipid, for example cationic cholesterol derivatives like TC-Chol (cholesteryl N-(trimethylammonioethyl) carbamate) or DC-Chol (cholesteryl N-(dimethylammonioethyl) carbamate). Most preferably the virosomes are IRIVs.

Procedures for the preparation of virosomes are well known to those of skill in the art (Bron et al., Methods Enzymol. 220: 313-331, 1993). Influenza virosomes, for example, can be reconstituted from the original viral membrane lipids and spike glycoproteins after solubilization of inactivated influenza virus with octaethyleneglycol monododecyl ether, sedimentation of the nucleocapsid (the viral glycoproteins and lipids will remain in the supernatant), and removal of the detergent in the supernatant with a hydrophobic resin (Bio-Beads SM2) (Stegmann et al., Traffic 1: 598-604, 1987). The IRIVs of the invention may also be CIRIVs, meaning that they contain hemagglutinin molecules from at least two different virus strains, for example from X-31 and A/Sing. The IRIVs of the invention can further contain cationic lipids, for example cationic cholesterol derivatives like cholesteryl N-(trimethylammonioethyl) carbamate chloride (TC-Chol) or cholesteryl N-(dimethylammonioethyl) carbamate chloride (DC-Chol).

Among other things, the present invention demonstrates that encapsulating a sample antigen in a liposome and combining said liposome-entrapped antigen with empty virosomes generates a potent immunogenic composition for CD8+ T (killer T) cells to create a potent adjuvant effect against the sample target antigen.

Therefore, a preferred embodiment of the present invention, suitable to trigger the cytotoxic immune response by activation of CD8+ cells, relates to a pharmaceutical composition comprising a virosome, preferably an IRIV, along with an antigenic peptide or protein of choice encapsulated in a carrier vehicle, preferably a liposome, said pharmaceutical composition being maintained at physiological pH.

In another preferred embodiment, the pharmaceutical compositions of the present invention serve to trigger a CD4+ helper T-cell response and, thus, comprise an antigen of choice coupled to (i.e. bound to) the surface of a carrier vehicle, preferably a liposome, and a virosome, preferably an IRIV.

In a further preferred embodiment, the pharmaceutical compositions of the present invention serve to induce a B cell response.

The pharmaceutical compositions according to the invention can optionally further comprise excipients, auxiliaries, additives, solvents and other pharmaceutically acceptable substances known to the person skilled in the art.

In the context of the present invention, the expression "pharmaceutically acceptable" refers to the fact that the administration of a certain compound, carrier, excipient and the like, is well tolerated by the recipient.

The use of the disclosed compositions for the manufacture of a medicament for vaccinating or inoculating a subject is also part of the present invention. Preferably said subject is a human. Alternatively, the disclosed pharmaceutical compositions may be used for therapeutic and/or prophylactic purposes.

Another aspect of the present invention relates to the use of a virosome, a liposome and at least one antigenic molecule for preparing a pharmaceutical composition for potentiating the immunogenicity of an antigen of choice (i.e. of an antigenic molecule), with the proviso that the pharmaceutical composition is maintained at physiological pH. In one embodiment, said antigen is encapsulated in or coupled to a liposome.

A method for eliciting or enhancing an immune response comprising the step of administering to a subject a pharmaceutical composition described above is also part of the present invention.

Another aspect of the invention relates to a kit of parts comprising a virosome, a liposome, and at least one antigenic molecule, wherein the kit additionally comprises means for maintaining the virosome, the liposome and/or the at least one antigenic molecule at physiological pH. In one specific embodiment, the kit according to the invention contains an empty virosome as an adjuvant, a carrier vehicle, for example a liposome, and optionally the desired antigenic molecule. All said compounds may be contained in separate vessels and may be in lyophilized form to facilitate the storage. If the kit comprises the virosome and carrier vehicle, for example a liposome, in the same solution, this solution is advantageously maintained at physiological pH. If the kit comprise the virosome and the carrier vehicle, for example a liposome and/or the antigenic molecule, in different solutions, each of these solutions is advantageously maintained at physiological pH, preferably at the same pH, such that this pH, or at least physiological pH as defined herein, is maintained upon combination of the individual solutions. In case one or more of the kit's compounds are lyophilized, the solvent for the solvation/reconstitution may also be included in the kit. In this case, the solvent for the solvation/reconstitution is advantageously maintained at physiological pH.

Administration

The present invention also provides for the administration of immunostimulatory pharmaceutical compositions. When administered, the compositions of the present invention are administered in pharmaceutically acceptable preparations. Such preparations may routinely contain pharmaceutically acceptable concentrations of salt, buffering agents, preservatives, compatible delivery vehicles, supplementary immune potentiating agents such as further conventional adjuvants and/or cytokines.

Such an immunogenic pharmaceutical composition can be administered in a wide variety of dosage forms and administration routes, all of which are well known to those of ordinary skill in the pharmaceutical arts.

Thus, the invention provides compositions for parenteral administration which comprise a solution of the antigenic molecules, virosomes and liposomes dissolved or suspended in an acceptable carrier, preferably an aqueous carrier, e.g., water, buffered water, 0.4% saline, 0.3% glycine, hyaluronic acid and the like known to a person skilled in the art. These compositions may be sterilized by conventional, well-known sterilization techniques, or may be sterile filtered. The resulting aqueous solutions may be packaged for use as is, or lyophilized, the lyophilized preparation being combined with a sterile solution maintained at physiological pH prior to administration.

The compositions of the invention may optionally contain pharmaceutically acceptable auxiliary substances as required to approximate physiological conditions, such as pH-adjusting and buffering agents, tonicity-adjusting agents, wetting agents and the like, for example, sodium acetate, sodium lactate, sodium chloride, potassium chloride, calcium chloride, sorbitan monolaurate, triethanolamine oleate, among many others known to a person skilled in the art. Actual methods for preparing parenterally administrable compounds will be known or apparent to those skilled in the art and are described in more detail in, for example, Remington: The Science and Practice of Pharmacy ("Remington's Pharmaceutical Sciences") by Gennaro A. R., ed. 20th edition, 2000: Williams & Wilkins P A, USA.

For parenteral administration, sterile suspensions and solutions are desired. Isotonic preparations that generally contain suitable preservatives are employed when intravenous administration is desired.

In the methods and uses of the present invention, the pharmaceutical compositions herein described in detail are typically administered in admixture with pharmaceutical diluents or excipients suitably selected with respect to the intended form of administration.

In preferred embodiments, the pharmaceutical compositions are administered intradermally, subcutaneously, or intramuscularly.

The pharmaceutical compositions of the present invention can be further supplemented by combining any of the above-mentioned compositions with a further immune response potentiating compound. Immune response-potentiating compounds are classified as either adjuvants or cytokines. Additional adjuvants may further enhance the immunological response by providing a reservoir of antigen (extracellularly or within macrophages), activating macrophages and stimulating specific sets of lymphocytes. Adjuvants of many kinds are well known in the art; specific examples include Freund's (complete and incomplete), components of the cells wall of mycobacterias (Bacillus calmette-guerin, *Mycobacterium vaccae, corynebacterium parvum*) Lipopolysaccharaides such as Lipid A, monophosphoryl Lipid A, LPS or LPS derivates or MF59 (Chiron), and various oil/water emulsions (e.g. IDEC-AF). Other currently used adjuvants include: mineral salts or mineral gels such as aluminium hydroxide, aluminium phosphate, and calcium phosphate, surface active substances such as lysolecithin, pluronic polyols, polyanions, keyhole limpet hemocyanins, and dinitrophenol, immunostimulatory molecules, such as saponins (QS-21 (SmithKline Beecham) ISCOMs), muramyl dipeptides and tripeptide derivatives, CpG dinucleotides, CpG oligonucleotides, lipopeptides/lipoproteins, cholera toxin and polyphosphazenes, particulate and microparticulate adjuvants, such as emulsions, cochleates, or immune stimulating complex mucosal adjuvants.

Cytokines are also useful in vaccination protocols as a result of lymphocyte stimulatory properties. Many cytokines useful for such purposes will be known to one of ordinary skill in the art, including interleukin-2 (IL-2), IL-12, GM-CSF, and many others.

Advantageously, suitable formulations of the present invention may be administered in a single dose, or the total dosage may be administered in divided doses for example of two, three, or four times.

The dosage regimen utilizing the pharmaceutical compositions of the present invention is selected in accordance with a variety of factors, including for example species, age, weight, sex and medical condition of the patient, the stage and severity of the condition to be treated, and the particular compound thereof employed, all of which can be readily determined by a physician of ordinary skill.

Initial doses can be followed by booster doses, following immunization protocols standard in the art.

The preparations (i.e. pharmaceutical compositions) of the invention are administered in effective amounts. Generally, doses of immunogens ranging from 1 nanogram/kilogram body weight to 100 milligrams/kilogram body weight, depending upon the mode of administration, are considered effective. The preferred range is believed to be between 500 nanograms and 500 micrograms per kilogram body weight. The absolute amount will depend upon a variety of factors, including the pharmaceutical composition selected for administration, whether the administration is in single or multiple doses, and individual patient parameters including age, physical condition, size, weight, and the stage of the disease. These factors are well known to those of ordinary skill in the art and can be addressed with no more than routine experimentation.

A further aspect of the invention relates to a pharmaceutical composition comprising a virosome, a liposome, and at least one antigenic molecule, wherein the pharmaceutical composition is maintained at physiological pH, for the vaccination or immunization of a subject. The at least one antigenic molecule is preferably entrapped in or bound to the liposome.

Yet another aspect of the invention relates to a pharmaceutical composition comprising a virosome, a liposome, and at least one antigenic molecule, wherein the pharmaceutical composition is maintained at physiological pH, for the treatment or prevention of a disease or disorder in a subject in need thereof. The at least one antigenic molecule is preferably entrapped in or bound to the liposome.

A still further aspect of the invention relates to a virosome, a liposome and at least one antigenic molecule, together maintained at physiological pH, for potentiating the immunogenicity of an antigenic molecule, with the proviso that said antigenic molecule is neither bound to, nor encapsulated in, nor otherwise associated with the virosome or virus-like particle.

It is the intention of the inventors that such variations are included within the scope of the invention.

EXAMPLES

The specific embodiments of the invention and the following examples are provided to demonstrate the efficiency of the claimed invention but are not to be interpreted as limiting the scope of the invention. To the extent that specific materials are mentioned, it is merely for purposes of illustration and is not intended to limit the invention. Unless otherwise specified, biochemical and molecular biology procedures, such as those set forth in Voet, Biochemistry, Wiley, 1990; Stryer, Biochemistry, W.H. Freeman, 1995; Bodanszky, Peptide Chemistry. A Practical Textbook, 2nd ed., Springer-Verlag, Berlin, 1993; Sambrook et al., Molecular Cloning, Cold Spring Harbor Laboratory, 2001; Ausubel et al. (Eds.), Current Protocols in Molecular Biology, John Wiley & Sons, 2000 are used. One skilled in the art may develop equivalent means or reactants without the exercise of inventive capacity and without departing from the scope of the invention.

It will be understood that many variations can be made in the compositions and procedures herein described while still remaining within the bounds of the present invention. It is the intention of the inventors that such variations are included within the scope of the invention.

Example 1

Reagents and peptides: Octaethyleneglycol-mono-(n-dodecyl)ether (OEG, $C_{12}E_8$), 1,2-Dipalmitoyl-sn-glycero-3-phospho-rac-(1-glycerol) (PG), Mitomycin C, L-Glutamine, Penicillin, Streptomycin, Hepes, penicillin and RPMI medium are purchased from Fluka Chemie GmbH and Sigma (Buchs, Switzerland), respectively. Sucrose (Eur. Phar.) is purchased from Merck (Dietikon, Switzerland). FCS was purchased from Gibco BRL (Basel, Switzerland). Egg phosphatidyl choline (PC) is obtained from Lipoid (Cham, Switzerland). 1-Oleoyl-3-palmitoyl-rac-glycero-2-phosphoethanolamine (PE) and peptides are obtained from Bachem (Bubendorf, Switzerland). Bio-Beads SM2 are purchased from Bio-Rad Laboratories (Glattbrugg, Switzerland). $Cr^{51}$ are obtained from Amersham Biosciences (Otelfingen, Switzerland). IL-2 is obtained from EuroCetus B.V. (Amsterdam, The Netherlands). N-succinimidyl-S-acetylthioacetate (SATA) is purchased from Pierce Biotechnology (Rockford, USA).

Influenza viruses of the A/Singapore/6/86 (A/Sing) strain and the X-31 strain, propagated in the allantoic cavity of embryonated eggs (Gerhard, W. 1976. The analysis of the monoclonal immune response to influenza virus. II. The antigenicity of the viral hemagglutinin. J. Exp. Med. 144:985-995), were obtained from Berna Biotech AG (Bern, Switzerland) and purified as described (Skehel, J. J. and Schild, G. C. 1971. The polypeptide composition of influenza A viruses. Virology 44:396). The hemagglutinin/phospholipid ratio was determined according to Böttcher (Böttcher, C. J. F., Van Gent, C. M., and Pries, C. 1961. A rapid and sensitive sub-micro phosphorus determination. Anal. Chim. Acta 24:203) and HA-quantification after SDS-PAGE with the Coomassie-extraction method as described by Ball (Ball, E. H. 1986. Quantitation of proteins by elution of Coomassie brilliant blue R from stained bands after sodium dodecyl sulfate-polyacrylamide gel electrophoresis. Anal. Biochem. 155:23).

Example 2

Preparation of the standard virosomes (IRIV): For a final volume of 4 ml, 32 mg egg PC and 8 mg PE are dissolved in 3 ml of PBS, 100 mM OEG (PBS/OEG). 2 mg HA of inactivated influenza A/Singapore/6/86 virus is centrifuged at 100,000× g for 1 h at 4° C. and the pellet is dissolved in 1 ml of PBS/OEG. The detergent solubilised phospholipids and viruses are mixed and sonicated for 1 min. This mixture is centrifuged at 100,000×g for 1 h at 18° C. and the supernatant is sterile filtered (0.22 μm). Virosomes are then formed by detergent removal using 1.25 g of wet SM2 Bio-Beads (Bio-Rad, Glattbrugg, Switzerland) for 1 h at room temperature with shaking and three times for 30 min with 0.625 g of Bio-Beads SM2 each.

Chimeric virosomes (CIRIV) containing HAs from X-31 and A/Sing were prepared similarly. Equal amounts of viral proteins from the two virus strains were mixed before solubilization.

Example 3

Preparation of liposomes with encapsulated specific peptide: 36.4 μmol (28 mg) PC and 15.6 μmol (11 mg) PG (molar ratio 70:30) are dissolved in methanol/chloroform (2:1). The solvent is removed by a rotary evaporator (Rotavapor R-205, Büchi Labortechnik, Switzerland) at 40° C. at a gradual vacuum of 30-10 kPa. The dried lipid film is hydrated with 350 μl PBS containing 2-3.5 mg of the specific peptide to be encapsulated. Before extrusion, the volume is adjusted to 500 μl with PBS. The liposome dispersion is then extruded ten times through polycarbonate membranes (Nucleopore Track-Etch membrane, 0.2 μm, Whatman, Kent, UK) with a 1.5 ml Lipex Extruder (Northern Lipids, Vancouver, Canada). Size determination of extruded liposomes is done by light scattering using a Zetasizer 1000HS instrument (Malvern Instruments, Worcestershire, UK).

Comparative Example 4

Preparation of peptide-CIRIVs as controls: CIRIVs (600 μl in PBS, approx. 6 mg phospholipid) are incubated with 200 μl (approx. 15 mg phospholipid) of PC/PG extruded liposomes (0.2 μm diameter) containing the specific peptide at 18° C. in PBS under constant stirring. The control peptide-CIRIVs are to be prepared as fusion products of liposomes and antigen-containing virosomes, in contrast to the present invention, in which liposomes and virosomes remain separate (i.e. unfused) in the composition. To trigger the fusion of the control CIRIVs, the pH is adjusted to 4.5-5.5 with 15 μl of 1 M HCl. After incubation for 30 min, the mixture is neutralized (pH 7.0-8.0) with 15 μl of 1 M NaOH and fusion products are extruded five times through polycarbonate membranes (Nucleopore Track-Etch membrane, 0.2 μm) with a 1.5 ml Lipex Extruder (Northern Lipids, Canada).

Example 5

Preparation of virosomes containing TC-Chol ("TIRIVs"): TIRIVs are prepared by the detergent removal method. For a final volume of 4 ml, 32 mg egg PC, 8 mg PE and 5 mg cholesteryl N-(trimethylammonioethyl)carbamate chloride (TC-chol) are dissolved in 2.6 ml of PBS, 100 mM OEG (PBS/OEG). 2 mg HA of inactivated A/Singapore/6/86 influenza virus is centrifuged at 100,000×g for 1 h at 4° C. and the pellet is dissolved in 1 ml of PBS/OEG. The detergent solubilised phospholipids and viruses are mixed with 0.4 mL of 50% (w/v) sucrose and sonicated for 1 min. This mixture is centrifuged at 100,000×g for 1 h at 18° C. and the supernatant is sterile filtered (0.22 μm). Virosomes are then formed by detergent removal using 1.25 g of wet Bio-Beads SM2 for 1 h at room temperature with shaking and five times for 30 min with 0.625 g of Bio-Beads SM2 each. The virosomes are sterile filtered (0.22 μm) and aliquoted in sterile glass vials. The closed vials are frozen at −70° C. and then lyophilized at −40° C. for 20 h and 10° C. for 2 h. The closed vials are stored at frozen until use.

Example 6

Preparation of peptide-TIRIVs: To obtain TIRIVs containing peptide of choice, the peptide is dissolved in water at the desired concentration. Frozen, lyophilized TIRIVs are removed from the freezer and equilibrated at RT for 2-5 min, before an equal amount of dissolved peptide (4° C.) are added to the lyophlisate. The vial is mixed shortly for about 10 sec on the vortex on intermediate level and stored at 4° C. until use. Alternatively, peptides which are linked to PE may be added to the TIRIVs during the preparation process described in example 5. The peptide is added at the desired concentration before sonication and sterile filtration of the solution. The other preparation steps remain unchanged. Reconstitution of the lyophilized TIRIVs is done with an equal volume of water.

Example 7

Immunizations: HLA-A2.1 tg mice were immunized subcutaneously (s.c.) with 100 μl of virosomes with encapsulated peptide, liposomes with encapsulated peptide together with empty virosomes, liposomes with encapsulated peptide, peptide with empty virosomes, peptide in saline solution, or empty virosomes. Mice received 2 injections at a 3-week interval and the response was analyzed 2 weeks after the last injection.

Example 8

Cytotoxicity assay: Spleen cells ($4\times10^6$/well) from individual immunized mice were restimulated for 5 days in 24-well tissue culture plates with $6\times10^5$ Mitomycin C treated (50 μg/ml for 1 hour) EL-4S3⁻Rob HHD that have been pulsed with 10 μg/ml specific peptide, in complete RPMI medium containing 2 mM L-Glutamine, 100 U/ml Penicillin, 100 μg/ml Streptomycin, 5 mM Hepes, 10% FCS and $5\times10^{-5}$ M 2-mercaptoethanol at 37° C. and 5% CO2. On day 2, 5 U/ml IL-2 were added. Specific cytolytic activity was tested in a standard $^{51}$Cr release assay against an EL-4S3⁻Rob HHD target cells pulsed with 10 μg/ml of specific peptide or medium control. After 4 hr incubation, $^{51}$Cr release was measured by using a γ-counter. Spontaneous and maximum release was determined from wells containing medium alone or after lysis with 1N HCl, respectively. Lysis was calculated by the formula: (release in assay−spontaneous release)/(maximum release−spontaneous release)×100. Peptide-specific lysis was determined as the percentage of lysis obtained in the presence or in the absence of peptide. Spontaneous release was always less than 15% of maximum release.

Example 9

Intracellular IFNγ staining: Spleen cells ($12\times10^6$) were incubated with 10 μg/ml specific peptide or non-relevant peptide (negative control) in complete RPMI medium containing 2 mM L-Glutamine, 100 U/ml Penicillin, 100 μg/ml Streptomycin, 5 mM Hepes, 5% FCS and $5\times10^{-5}$ M 2-mercaptoethanol at 37° C. and 5% CO2 in the presence of 5 μg/ml Brefeldin A for 4 h. Cells were stained with FITC-conjugated anti-CD8 antibodies, permeabilized, and stained with PE-conjugated anti-IFNγ antibodies using the Cytofix/Cytoperm kit following the manufacturer's instructions (BD Pharmingen, San Diego, USA). Data were acquired on a FACSCalibur flow-cytometer and analyzed with WinMDI2.8 software. Frequency of IFNγ-producing cells was calculated as percentage of IFNγ positive and CD8 positive cells among total CD8 positive cells. The percentage of peptide-specific cells was obtained by subtracting the percentage in samples stimulated with non-relevant peptide from the percentage in samples stimulated with specific peptide.

Example 10

ELISPOT assay: To quantify the frequency of epitope-specific IFNγ-producing cells we used the IFNγ ELISPOT kit from U-CyTech (Utrecht, Netherlands). Spleen cells ($6\times10^6$/well) from immunized mice were restimulated in 24-well tissue culture plates with 10 μg/ml specific peptide or a non-relevant peptide (negative control) in complete RPMI medium containing 2 mM L-Glutamine, 100 U/ml Penicillin, 100 μg/ml Streptomycin, 5 mM Hepes, 10% FCS and $5\times10^{-5}$ M 2-mercaptoethanol at 37° C. and 5% CO2. After overnight stimulation $10^5$ and $10^4$ cells from the restimulation cultures were transferred in duplicates to a precoated and albumin-blocked IFNγ ELISPOT plate (U-CyTech, Utrecht, Netherlands) and incubated for 5 h at 37° C. to allow cytokine secretion. Spots were developed following the manufacturer's instructions and were counted by using a microscope. The background level was assessed in wells where effector cells were stimulated with splenocytes pulsed with non-relevant peptide. The number of peptide-specific spots was obtained by subtracting the background from the number of spots induced after specific peptide stimulation.

Example 11

HCV Core 132 peptide quantification was performed by reversed phase-HPLC on an Agilent 1100 Series system (Agilent Technologies) equipped with a ZORBAX Eclipse XDB C8, 4.6×150 mm, 5 μm reversed phase column (Agilent Technologies), a column oven set at 25° C. and a DAD detector set at 210 nm. The elution was occurred by a gradient consisting triethylammoniumphosphate 10 mmol/l pH 3 in water as mobile phase A (reagents from Merck) and acetonitrile as mobile phase B (acetonitrile from Sigma). The gradient runs from 25% B to 38% B over 7 min and from 38% B to 100% B over 5.4 min where it stays for other 4 min by a flow of 1.3 ml/min. The injection volume was 10 μl. For quantification of encapsulated peptide, a fraction (5-30 μl) of liposomes or virosomes, respectively, was loaded on freshly prepared, PBS-equilibrated 1 ml Sephadex G50 Coarse gel-filtration spin columns. Vesicles with encapsulated peptide only were obtained after centrifugation of the spin column at 300×g for 2 min, as the non-encapsulated peptide was retarded in the column. For spiking experiments, a defined amount of peptide was added to empty liposomes before purification.

Example 12

Chimeric virosomes with HA from the X-31 and the A/Sing Influenza strain, respectively, were prepared as described in example 2 with addition of 4 mg biotin-DHPE (biotin-DHPE (N-(biotinoyl)-1,2-dihexadecanoyl-sn-glycero-3-phosphoethanolamine, triethylammonium salt, Molecular Probes Europe, Leiden, The Netherlands) to the phospholipid mixture (CIRIVBio with 1 mg/ml biotin-DHPE). HCV Core132 Peptide containing liposomes were prepared as described in example 3. HCV Core132 Peptide containing CIRIVBio were prepared as described in example 4 with CIRIVBio instead of regular CIRIVs. For affinity precipitation 5 μl of Peptide-CIRIVBio were added to IP buffer (50 mM sodium phosphate, 0.1 M NaCl, pH 7.5) to a final volume of 200 μl. Peptide-liposomes (equal amount of peptide as Peptide-CIRIVBio) were mixed with 5 μl of empty CIRIVBio, in a volume of 200 μl. 100 μl of Streptavidin paramagnetic beads (Dynabeads MyOne™ Streptavidin (10 mg/ml), Dynal Biotech, Hamburg, Germany). were washed twice in IP buffer and incubated with the sample mixtures at 4° C. for 1.5 h with continuous shaking. The precipitate was washed twice in IP buffer and resuspended in 25 μl OEG-PBS. After incubation at 4° C. for 5 min, the beads were removed and the supernatant was analysed by RP-HPLC as described in example 11.

Example 13

Preparation of empty liposomes: 36.4 μmol (28 mg) PC and 15.6 μmol (11 mg) PG (molar ratio 70:30) are dissolved in methanol/chloroform (2:1). The solvent is removed by a rotary evaporator (Rotavapor R-205, Büchi Labortechnik, Switzerland) at 40° C. at a gradual vacuum of 30-10 kPa. The dried lipid film is hydrated with 500 µl PBS. The liposome dispersion is then extruded ten times through polycarbonate membranes (Nucleopore Track-Etch membrane, 0.2 µm, Whatman, Kent, UK) with a 1.5 ml Lipex Extruder (Northern Lipids, Vancouver, Canada). Size determination of extruded liposomes is done by light scattering using a Zetasizer 1000HS instrument (Malvern Instruments, Worcestershire, UK).

Example 14

Preparation of liposomes with encapsulated specific protein: 36.4 µmol (28 mg) PC and 15.6 µmol (11 mg) PG (molar ratio 70:30) are dissolved in methanol/chloroform (2:1). The solvent is removed by a rotary evaporator (Rotavapor R-205, Büchi Labortechnik, Switzerland) at 40° C. at a gradual vacuum of 30-10 kPa. The dried lipid film is hydrated with 250-350 µl PBS containing 2-10 mg of the specific protein to be encapsulated. Before extrusion, 100-300 µL of PBS is added to the liposomes. The liposome dispersion is then extruded ten times through polycarbonate membranes (Nucleopore Track-Etch membrane, 0.2 µm, Whatman, Kent, UK) with a 1.5 ml Lipex Extruder (Northern Lipids, Vancouver, Canada). Size determination of extruded liposomes is done by light scattering using a Zetasizer 1000HS instrument (Malvern Instruments, Worcestershire, UK).

Example 15

Preparation of liposomes to which peptide is bound (peptide-liposomes): For a final volume of 4 ml, 32 mg egg PC, 8 mg PE and the wanted amount of the peptide-PE (e.g. UK39) conjugate are dissolved in 4 ml of PBS, 100 mM OEG (PBS/OEG). The detergent solubilised phospholipids and the peptide are mixed and sonicated for 1 min. This mixture is centrifuged at 100,000×g for 1 h at 18° C. (optional: sterile filtration (0.22 µm)). Liposomes are then formed by detergent removal using 1.25 g of wet SM2 Bio-Beads (BioRad, Glattbrugg, Switzerland) for 1 h at room temperature with shaking and three times for 30 min with 0.625 g of Bio-Beads SM2 each. Finally, the peptide-liposome solution (e.g. UK39-liposome) is sterile filtered (0.22 µm) and stored at 4° C.

Example 16

Immunizations: HLA-A2.1 tg mice were immunized subcutaneously (s.c.) with 100 µl of liposomes with encapsulated peptide; virosomes with encapsulated peptide (CIRIV); liposomes with encapsulated peptide mixed with empty virosomes; virosomes with encapsulated peptide (CIRIV) mixed with empty liposomes; liposomes with encapsulated peptide (site 1) and empty virosomes (site 2) injected separately at different sites; or empty virosomes. Mice received 2 injections at a 3-week interval and the response was analyzed 2 weeks after the last injection.

Example 17

Immunizations: C57Bl/6 mice were immunized subcutaneously (s.c.) with 100 µl of liposomes with encapsulated protein, liposomes with encapsulated protein mixed with empty virosomes, or empty virosomes. Mice received 2 injections at a 3-week interval and the response was analyzed 2 weeks after the last injection.

Example 18

Immunizations: HLA-A2.1 tg mice were immunized subcutaneously (s.c.) with 100 µl of liposomes with encapsulated peptide; liposomes with encapsulated peptide mixed with empty virosomes; or liposomes with encapsulated peptide mixed with HBsAg antigen. Mice received 2 injections at a 3-week interval and the response was analyzed 2 weeks after the last injection.

Example 19

Immunizations: HLA-A2.1 tg mice were immunized subcutaneously (s.c.) with 100 µl of liposomes with encapsulated peptide; or liposomes with encapsulated peptide mixed with different amounts of empty virosomes. Mice received 2 injections at a 3-week interval and the response was analyzed 2 weeks after the last injection.

Example 20

Immunizations: Balb/c mice were immunized intramuscularly (i.m.) with 100 µl of liposomes to which peptide is bound; liposomes to which peptide is bound mixed with empty virosomes; or liposomes to which peptide is bound (site 1) and empty virosomes (site 2) were injected separately at different sites. Mice received 3 injections at a 3-week interval and the sera were taken 2 weeks after the last injection.

Example 21

Cytotoxicity assay for ovalbumin protein immunized mice: Spleen cells ($4 \times 10^6$/well) from individual immunized mice were restimulated for 5 days in 24-well tissue culture plates with $6 \times 10^5$ Mitomycin C treated (50 µg/ml for 1 hour) EG.7OVA cells in complete RPMI medium containing 2 mM L-Glutamine, 100 U/ml Penicillin, 100 µg/ml Streptomycin, 5 mM Hepes, 10% FCS and $5 \times 10^{-5}$ M 2-mercaptoethanol at 37° C. and 5% CO2. On day 2, 5 U/ml IL-2 were added. Specific cytolytic activity was tested in a standard $^{51}$Cr release assay against an EL-4 target cells pulsed with 10 µg/ml of the OVA 257 peptide or medium control. After 4 hr incubation, $^{51}$Cr release was measured by using a γ-counter. Spontaneous and maximum release was determined from wells containing medium alone or after lysis with 1N HCl, respectively. Lysis was calculated by the formula: (release in assay−spontaneous release)/(maximum release−spontaneous release)×100. Peptide-specific lysis was determined as the percentage of lysis obtained in the presence or in the absence of peptide. Spontaneous release was always less than 15% of maximum release.

Example 22

Intracellular IFNγ staining for ovalbumin protein immunized mice was performed as described in Example 9 using the OVA 257 peptide as specific peptide for stimulation.

Example 23

Enzyme-linked immunosorbent assay (ELISA) analyses with peptidephosphatidylethanolamine conjugates: Polysorp plates (Nunc, Fisher Scientific, Wohlen, Switzerland) were coated overnight at 4° C. with 100 µl of a 10 µg/ml solution of peptide-phosphatidylethanolamine conjugate in PBS (pH 7.4). Wells were then blocked with 5% milk powder in PBS for 2 h at RT, followed by three washes with PBS containing 0.05% Tween 20. Plates were then incubated with serial dilutions of the mouse serum in PBS containing 0.05% Tween 20 and 0.5% milk powder for 2 h at 37° C. After being washed, plates were incubated with HRP-conjugated goat anti-mouse Ig antibody (BD Bioscience, Basel, Switzerland) for 1 h at 37° C. After being washed again, OPD-substrate (O-Phenylendiamine tablets, Fluka, Buchs, Switzerland, 1 tablet in 50 ml citrate buffer+50 µl H2O2) was added, and the plates were incubated in the dark at room temperature until the calorimetric reaction had progressed sufficiently and reaction was stopped by addition of 100 µl 1 M H2SO4 and optical densities (OD) were read at 492 nm on a Spectra Max Plus (Molecular Devices, Bucher Biotech, Basel, Switzerland).

Example 24

Peptide quantification of UK39: Peptide quantification is performed by reversed phase-HPLC on an Agilent 1100 Series system (Agilent Technologies) equipped with a ZORBAX Eclipse XDB C8, 4.6×150 mm, 5 µm reversed phase column (Agilent Technologies), a sample cooler set at 4° C. and a DAD detector set at 210 nm. As mobile phase A 0.1% trifluoroacetic acid in water and as mobile phase B 0.1% trifluoroacetic acid in methanol (reagents from sigma) are used. The gradient runs from 60% B to 100% B over 15 min with additional 5 min at 100% B and a flow of 1 ml/min at 60° C. The injection volume is 100 µl.

Example 25

Ovalbumin protein quantification: Protein quantification is performed by reversed phase-HPLC on an Agilent 1100 Series system (Agilent Technologies) equipped with a Jupiter Proteo 90A, 4.6×150×2.5 reversed phase column (Phenomenex), a sample cooler set at 4° C. and a DAD detector set at 280 nm. As mobile phase A, 0.1% trifluoroacetic acid in water and as mobile phase B 0.1% trifluoroacetic acid in acetonitrile (all reagents from Sigma) are used. The gradient runs from 35% B to 80% B over 10 min and from 80% B to 100% B over 0.01 min with additional 10 min at 100% B and a flow of 1.0 ml/min at 45° C. The injection volume is 100 µl.

Example 26

In addition to examples 2 and 5, virosomes are prepared with other influenza virus strains (e.g. with antigenic subtypes H1N1 or H3N2) obtained from Berna Biotech AG (Switzerland). Tetanus toxoid was obtained from Shanta Biotech (India). Hepatitis B surface antigen (HBsAg) was obtained from Berna Biotech AG (Switzerland). Chicken egg albumin (ovalbumin protein) was purchased from Sigma (Switzerland).

The invention claimed is:

1. A pharmaceutical composition comprising a virosome, a liposome, and at least one antigenic molecule, wherein the pharmaceutical composition is maintained at physiological pH, wherein said at least one antigenic molecule is entrapped in or bound to said liposome, further wherein said virosome and said liposome remain as separate entities at said physiological pH.

2. The pharmaceutical composition according to claim 1, wherein said at least one antigenic molecule is bound to the surface of the liposome via a lipophilic anchor molecule.

3. The pharmaceutical composition of claim 1, wherein said at least one antigenic molecule is selected from the group consisting of peptides, proteins, lipids, mono-, oligo- and polysaccharides, glycopeptides, carbohydrates, lipopeptides, bacterial or viral pathogens and toxins, other small immunogenic molecules and DNA/RNA coding for such molecules.

4. The pharmaceutical composition of claim 1, further comprising pharmaceutically acceptable excipients, auxiliaries, additives, preservatives, buffering agents, or solvents.

5. The pharmaceutical composition of claim 1 further comprising an additional immune potentiating agent, selected from the group consisting of adjuvants and cytokines.

6. The pharmaceutical composition of claim 1, wherein the virosome is an immunopotentiating reconstituted influenza virosome (IRIV).

7. The pharmaceutical composition according to claim 6, wherein the IRIV is a chimeric IRIV (CIRIV).

8. The pharmaceutical composition according to claim 6, wherein the virosome further contains cationic lipids.

9. The pharmaceutical composition according to claim 8, wherein said cationic lipid is a cationic cholesterol derivative.

10. The pharmaceutical composition according to claim 9, wherein the cationic cholesterol derivative is DC-Choi or TC-Chol.

11. The pharmaceutical composition according to claim 1, wherein said composition is lyophilized.

12. A method of vaccinating or immunizing a subject, said method comprising administering a pharmaceutical composition comprising a virosome, a liposome, and at least one antigenic molecule for the vaccination or immunization of said subject, wherein the pharmaceutical composition is maintained at physiological pH, wherein said at least one antigenic molecule is entrapped in or bound to said liposome, further wherein said virosome and said liposome remain as separate entities at said physiological pH.

13. A method of treating or preventing a disease or disorder in a subject, said method comprising administering a pharmaceutical composition comprising a virosome, a liposome, and at least one antigenic molecule to said subject in need thereof, wherein the pharmaceutical composition is maintained at physiological pH, wherein said at least one antigenic molecule is entrapped in or bound to said liposome, further wherein said virosome and said liposome remain as separate entities at said physiological pH.

14. The method of claim 12, wherein said subject is a mammal.

15. The method of claim 14, wherein said mammal is a human.

16. A method of potentiating the immunogenicity of an antigenic molecule, said method comprising preparing a pharmaceutical composition comprising a virosome, a liposome and at least one antigenic molecule wherein said pharmaceutical composition is maintained at physiological pH, wherein said at least one antigenic molecule is entrapped in or bound to said liposome, further wherein said virosome and said liposome remain as separate entities at said physiological pH.

17. The method of claim 16, wherein said antigenic molecule is encapsulated in or bound to the surface of said liposome.

18. A kit of parts comprising a virosome, a liposome, and at least one antigenic molecule, wherein the kit additionally comprises means for maintaining the virosome, the liposome and/or the at least one antigenic molecule at physiological pH, wherein said virosome and said liposome remain as separate entities at said physiological pH.

19. The kit of claim 18, wherein at least one of the virosome, the liposome, the at least one antigenic molecule and the means for maintaining physiological pH are each contained in separate vessels; or the virosome, the liposome, the at least one antigenic molecule and the means for maintaining physiological pH are contained in the same vessel.

20. The kit of claim 18, wherein at least one of the virosome, the liposome and the at least one antigenic molecule is lyophilized.

21. The kit of claim 20, wherein said kit further comprises a reconstitution solvent for the lyophilized compounds.

22. A method for the vaccination or immunization of a subject, said method comprising administering a pharmaceutical composition to said subject, said composition comprising a virosome, a liposome, and at leak one antigenic molecule, wherein said pharmaceutical composition is maintained at physiological pH, wherein said subject is a human, wherein said composition is administered to said subject in an amount sufficient to elicit a protective immune response in said subject, wherein said at least one antigenic molecule is entrapped in or bound to said liposome, further wherein said virosome and said liposome remain as separate entities at said physiological pH.

23. A method for the treatment or prevention of infectious diseases and/or cancer in a subject, said method comprising administering a therapeutically effective amount of a pharmaceutical composition to said subject, said composition comprising a virosome, a liposome, and at least one antigenic molecule, wherein said pharmaceutical composition is maintained at physiological pH, wherein said at least one antigenic molecule is entrapped in or bound to said liposome, further wherein said virosome and said liposome remain as separate entities at said physiological pH, further wherein said subject is a human.

24. The method according to claim 22, wherein the administration route is non-parenteral selected from intramuscular, intradermal or subcutaneous injection.

25. A method for the preparation of a pharmaceutical composition according to claim 1, comprising the steps of a) providing a virosome and an antigenic molecule entrapped in or bound to a liposome; and b) forming a mixture of said components in a pharmaceutically acceptable excipient or solvent maintained at physiological pH.

26. A virosome, a liposome and at least one antigenic molecule, together maintained at physiological pH, for potentiating the immunogenicity of an antigenic molecule, with the proviso that said antigenic molecule is neither bound to, nor encapsulated in, nor otherwise associated with the virosome.

* * * * *

UNITED STATES PATENT AND TRADEMARK OFFICE
CERTIFICATE OF CORRECTION

PATENT NO. : 8,496,962 B2  
APPLICATION NO. : 12/086315  
DATED : July 30, 2013  
INVENTOR(S) : Rinaldo Zurbriggen et al.

Page 1 of 1

It is certified that error appears in the above-identified patent and that said Letters Patent is hereby corrected as shown below:

In the Claims:

Column 25, lines 8-19, please amend claim 22 to read:

-- 22. A method for the vaccination or immunization of a subject, said method comprising administering a pharmaceutical composition to said subject, said composition comprising a virosome, a liposome, and at least one antigenic molecule, wherein said pharmaceutical composition is maintained at physiological pH, wherein said subject is a human, wherein said composition is administered to said subject in an amount sufficient to elicit a protective immune response in said subject, wherein said at least one antigenic molecule is entrapped in or bound to said liposome, further wherein said virosome and said liposome remain as separate entities at said physiological pH. --

Signed and Sealed this  
Twelfth Day of November, 2013

Teresa Stanek Rea  
*Deputy Director of the United States Patent and Trademark Office*